United States Patent [19]

Gratton et al.

[11] Patent Number: 5,492,118
[45] Date of Patent: Feb. 20, 1996

[54] DETERMINING MATERIAL CONCENTRATIONS IN TISSUES

[75] Inventors: Enrico Gratton; John Maier; Maria A. Franceschini; Sergio Fantini; Scott A. Walker, all of Urbana, Ill.

[73] Assignee: Board of Trustees of the University of Illinois, Chicago, Ill.

[21] Appl. No.: 253,935

[22] Filed: Jun. 3, 1994

Related U.S. Application Data

[63] Continuation-in-part of Ser. No. 168,813, Dec. 16, 1993.
[51] Int. Cl.$^6$ ................................................ A61B 5/00
[52] U.S. Cl. ......................... 128/633; 128/664; 128/666; 356/41; 356/338; 250/341.1
[58] Field of Search ...................... 128/633–634, 128/664–666; 250/341.1, 341.3, 343, 339.1; 356/41, 338, 446

[56] References Cited

U.S. PATENT DOCUMENTS

| | | |
|---|---|---|
| 4,840,485 | 6/1989 | Gratton . |
| 4,972,331 | 11/1990 | Chance . |
| 5,032,024 | 7/1991 | Cope . |
| 5,122,974 | 6/1992 | Chance ................................ 128/633 |
| 5,167,230 | 12/1992 | Chance . |
| 5,187,672 | 2/1993 | Chance et al. . |
| 5,188,108 | 2/1993 | Secker ................................. 128/633 |
| 5,209,231 | 5/1993 | Cote et al. ........................... 128/633 |
| 5,212,386 | 5/1993 | Gratton et al. . |
| 5,213,105 | 5/1993 | Gratton et al. . |
| 5,243,983 | 9/1993 | Tarr et al. ............................ 128/633 |
| 5,267,152 | 11/1993 | Yang et al. ........................... 128/633 |
| 5,331,958 | 7/1994 | Oppenheimer ...................... 128/633 |
| 5,402,778 | 4/1995 | Chance ................................ 128/633 |

FOREIGN PATENT DOCUMENTS

| | | |
|---|---|---|
| 0497021A1 | 8/1992 | European Pat. Off. . |
| 2228314 | 2/1989 | United Kingdom . |
| WO90/09003 | 8/1989 | WIPO . |
| WO94/10901 | 5/1994 | WIPO . |

OTHER PUBLICATIONS

Article by J. R. Lakowicz et al. entitled Frequency–domain fluorescence spectroscopy, a new method for the resolution of complex fluorescence emission, from Trends in Analytical Chemistry Nov., 1986 pp. 257–263.

Article entitled: "Time–Resolved Spectroscopy of the Human Forearm" by Ferrari et al.—J. Photochem. Photobiol. B: Biol., 16 (1992) 141–153.

Article entitled: "Tissue Characterization and Imaging Using Photon Density Waves" by Svaasand et al.—Optical Engineering, Feb., 1993, vol. 32 No. 2, pp. 258–265.

Article by Patterson et al. by Applied Optics, vol. 30, No. 31, pp. 4474–4476 entitled: "Frequency–Domain Reflectance for the Determination of the Scattering and Absorption Properties of Tissue", 1 Nov., 1991.

Article by Patterson et al. by Applied Optics, vol. 28, No. 12, pp. 2331–2336 entitled: "Time Resolved Reflectance and Transmittance for the Non–Invasive Measurement of Tissue Optical Properties", 15 Jun., 1989.

*Primary Examiner*—Angela D. Sykes
*Assistant Examiner*—Robert L. Nasser, Jr.
*Attorney, Agent, or Firm*—Gerstman, Ellis & McMillin, Ltd.

[57] ABSTRACT

The relative concentration of a material such as glucose in a turbid medium such as living tissue may determining the scattering coefficient of the light that has passed through the turbid medium; and comparing the scattering coefficient with a previous scattering coefficient determined with respect to the turbid medium.

25 Claims, 4 Drawing Sheets

DETERMINING MATERIAL CONCENTRATIONS IN TISSUES

CROSS REFERENCE TO RELATED APPLICATION

This is a continuation-in-part of Gratton, et al. application Ser. No. 08/168,813, filed Dec. 16, 1993.

BACKGROUND OF THE INVENTION

The determination of the optical properties of tissues is of fundamental importance in many fields of medicine, both for diagnostic and monitoring purposes. It is well known that light of differing wavelengths penetrates differently in various tissues. In the near infrared region, for example, (about 650 nm to about 1000 nm), light of this wavelength penetrates several centimeters through tissue. It is intended that the term "light" includes visible light and other electromagnetic radiation as well which is invisible to the human eye, for example, infrared and ultraviolet.

Because of the capability of various forms of light to penetrate tissue for several centimeters, photometric or spectroscopic methods can be used to measure the concentration of tissue metabolites such as hemoglobin by the measuring of the absorption of the light at one or more wavelengths.

In the prior art, the absolute determination of the concentration of a substance can be obtained by the measurement of the light transmitted through a sample of known thickness. Such a transmission measurement enables one to determine the absorption coefficient. Using this, the concentration of the measured substance can be calculated using the molar extinction coefficient of that substance via the Beer-Lambert law.

In the event of interference caused by more than one substance being present, measurement at different wavelengths can provide a method to determine the concentration of one or more different chemical species present, assuming that the materials present have different absorption spectra. The success of this method depends on the precision of the measurement and on the number of different substances present.

Additional problems arise in the photometry of tissues and other materials having high turbidity, such as emulsions. For purposes of this disclosure, it is to be understood that the term "tissue" may include living materials, but can also include non-living materials such as emulsions when it is desired to obtain similar data from such emulsions as is done by this invention with tissues. A measurement of the light transmitted through a slab of tissue has in the prior art been not practical, using non-invasive methods, except for special, thin regions of the body where light can shine entirely through the tissue and be detected on the other side. An example of this is a clinically used photometric blood oxygen sensor, which fits on the finger tip and shines directly therethrough to give real time oxygen concentration data.

An exception to this is found in Gratton, et al. patent application Ser. No. 08/168,813, filed Dec. 16, 1993, cited above, in which a method and apparatus is provided for quantitative measurement of blood oxygen saturation by photometry of the arm, thigh, or the like.

In tissue photometry, the amount of transmitted light depends not only on the absorption of the medium being analyzed, but also on the scattering properties thereof. This light scattering greatly increases the complexity of photometric analysis of tissue, emulsions, and similar materials, since light scattering produces an unpredictable variation of the amount of light transmitted, which can vary significantly between various samples of tissues and the like.

Many different methods have been proposed to deal with this problem of scattering in photometric processes. For example, empirical corrections based on the type of tissue to be measured have been used to account for the effect of scattering on the absorption properties. For reflection measurements, theoretical models have been used to calculate the albedo of a surface. The success of all of these models has been poor, although there are commercially available instruments based upon those principles. A major problem is that in order to obtain a reasonable estimate of the concentration of a substance in tissue, some sort of a priori calibration must be performed, based on a statistical analysis of a large number of corresponding tissue samples. However, the range of variation of scattering within tissues from various individuals results in fundamentally unpredictable results, with the photometric results being strongly modified by factors such as skin color, and the amount of lipids in muscles.

The Hamamatsu Company of Japan in 1990 introduced a simple tissue spectrometer called NIRO 500 for the measurement of tissue oxygenation and total blood volume for neonatal monitoring. The principles of this device are as disclosed in Cope U.S. Pat. No. 5,032,024. The instrument is a steady state instrument, and is based on four different laser diodes emitting in the near infrared range. The light is brought to the tissue using a fiber optic system. The measurement is purely a steady-state one, with the optical path length in the tissue being not measurable. Thus, only relative quantities can be obtained, rather than absolute concentrations of materials being measured.

Some materials such as glucose lack a strong absorption line at a convenient wavelength of light which can be used for photometric determination through tissue. In this circumstance, the problem of photometrically determining concentrations of glucose or other metabolites in tissue or materials in an emulsion becomes quite difficult.

By this invention, a method is provided in which the concentration of an ingredient of a highly scattering medium, for example glucose in tissue, can be determined and monitored in real time on a relative concentration basis by a photometric technique in which no band of the light is strongly absorbed by the material being monitored.

DESCRIPTION OF THE INVENTION

In accordance with this invention, one may determine the relative concentration of a material in a turbid medium such as tissue of a patient by a method which comprises: shining light through said turbid medium; determining the scattering coefficient of said light that has passed through said turbid medium; and comparing said scattering coefficient with a previous scattering coefficient determined with respect to said tissue.

It has been found that many materials in turbid media will cause the scattering coefficient of light through said turbid medium to vary as the concentration of the material varies. Specifically, the concentration of glucose in the tissue of a living patient is capable of such monitoring. The process preferably works for solutes in the aqueous phase of living tissue, or in the aqueous phase of an emulsion. The process is particularly advantageous in those circumstances where it is not convenient to do the photometric measurement at a wavelength which the solute strongly absorbs.

Thus, the glucose level of a patient can be monitored by the photometric method of this invention. The method may not be quantitative, so that it is most desirable to compare the results with a base line of scattering coefficient data determined upon the same tissue of the patient, or any other sample for measuring. Thus, a normal scattering coefficient can be determined, so that future measurements can monitor, for example, the glucose level of a diabetic patient by the simple application of a light cell and sensor to the skin of the patient, for example the thigh, forearm, or stomach. Any perceived change in the scattering coefficient away from the base line value is an indication of a change in the glucose content, to serve as a warning to the patient that action needs to be taken.

One may preferably analyze for the presence and concentration of such a substance in a highly turbid medium such as tissue of a patient by the steps of: sequentially illuminating and shutting off a plurality of light sources which are spaced at different distances from a light sensor, while modulating the intensity of light from said light sources at a first frequency and passing said modulated light through the turbid sample and then to said sensor. One also provides a signal to the light sensor which is coherent with the modulated light, at a second frequency, to modulate the gain of, or multiply the output of, the light sensor by the coherent signal, the second frequency being different from the first frequency. One then derives a resultant signal from the sensor while receiving the modulated light, the resultant signal being at a frequency of the difference between the first and second frequencies. From this, it becomes possible to detect at least two of the following characteristics of the modulated light sensed by the sensor: that is the phase shift component, the DC component, and the AC component. These are compared with the corresponding components of the modulated light as it is originally emitted by the light sources.

The terms "DC component" and "AC component" define differing portions of the amplitude of the light from the light sources. Specifically, as previously described, the light from the light sources is of amplitude modulated intensity, so that it becomes brighter and dimmer in a cycle at the first frequency. This frequency is typically very high (e.g. 80 to 200 MHz) so that the fluctuation of light intensity is invisible to the eye. The AC component of the light comprises the change in light intensity from the peak of the cycle to the trough of the cycle; that is, the maximum change in the amplitude of the light intensity as it goes through its rapid cycle of amplitude modulation. The DC component is that portion of the light intensity measured from zero to the minimum intensity that the light always possesses, which of course is found at the bottom of the troughs of the wave pattern imposed on the light by the amplitude modulation.

Therefore, the maximum intensity of the light signal, found at the top of each wave, is the sum of the DC and AC light components. The minimum intensity of the light in its amplitude modulated cycle is the DC component alone.

In accordance with this invention, as the amplitude modulated light passes through human tissue or another highly turbid material to the sensor, the phase of the amplitude modulated light signal will shift, and the DC and AC components will attenuate. From this information, it is possible to obtain quantitative information as to at least relative concentrations of certain materials present in the tissue on a real time or moment-by-moment basis.

This is preferably accomplished by sequentially turning on and off the plurality of light sources which are at differing distances from the light sensor. Thus, by the data provided from each of these plural light sources of differing distances, differing values for phase shift, DC component, and/or AC component may be determined separately for each light source to compute linear graphical data having characteristic slopes. Once the slopes are known, the value of the scattering coefficient at the wavelength of the light used can be computed. From this value, particularly at two different wavelengths, at least relative concentrations of materials present such as glucose can be calculated, by comparing with a known glucose concentration baseline and its scattering coefficient.

The concentration of materials such as glucose can be determined by monitoring changes in the scattering coefficient. The scattering coefficient can be determined without the material being analyzed having a characteristic strong absorption band at the wavelength of light used. Without wishing to be held to any particular theory of operation of the invention of this application, it is believed that the scattering coefficient depends upon the concentration of the glucose or other material being tested in the highly scattering medium such as tissue. A change in the concentration of the glucose present changes the index of refraction of the aqueous portion of the highly scattering medium. For example, if the concentration of glucose present in an aqueous fat emulsion is being monitored, the fat phase of the emulsion may have an index of refraction of, say 1.42, which is the index of refraction of soybean oil. The index of refraction of the water phase of the emulsion is about 1.33. The index of refraction of water containing differing concentrations of glucose will vary through a range, causing the scattering characteristics of the overall emulsion to vary. Thus the scattering coefficient of the turbid medium varies with the concentration of glucose present.

When the index of refraction of the aqueous medium matches the index of refraction of the suspended particles, scattering ceases to exist. Thus, if the index of refraction of the scattering particles in a medium is constant, the scattering coefficient of the medium becomes a function of the index of refraction of the remaining portion of the medium. Thus the concentration of the glucose or other material in the aqueous portion of a scattering medium can be determined from the scattering coefficient, either by comparison with base line data, or tables of precalculated measurements in the case of simpler emulsions.

Typically, in view of the variability of the scattering characteristics of different samples of tissue, one uses baseline data taken on the very same tissue so that relative changes in the concentration of glucose or another material can be monitored by comparison with that baseline data. Thus a diabetic patient, for example, can monitor his blood sugar concentration by simply applying a photometry head to the same part of his body on a repeated basis, for example the thigh or the forearm. The scattering coefficient can be computed with every reading through software in the photometry apparatus. Any change in the scattering coefficient can be indicated by some conventional alarm mode to give a diabetes patient, for example the opportunity to frequently monitor himself or herself throughout the day for any changes in the blood sugar level.

The calculation of the scattering coefficient can be accomplished in very short order through a microprocessor or the like, so that these values can be displayed in real time to a physician or nurse simply by applying a sensor head to the skin of a patient, without any need for the light to pass entirely through the tissue of the patient to the other side.

The sensor for detecting light in this invention can detect scattered light in the tissue, so that the light paths from the light sources to the sensor do not have to be linear. In fact, the direction of light emission and the general direction of light sensing may be parallel, as illustrated by the specific embodiment of the sensor head disclosed herein.

Preferably, the sensor for detecting light used herein may also carry the light sources in a common sensor head along with the sensor, plus a shield to prevent the direct access of light from the light sources to the light sensor without passing through the tissue of the patient.

The sensor instrument of this invention may carry an electronic processor for computing the slopes of at least two of the phase shift, the DC, and the AC components which are determined from each of the plurality of light sources of differing distances. From this, the processor can compute the scattering coefficient of the tissue. A relative concentration of glucose or the like present in the tissue may be computed. The sensor instrument may then have means for displaying such concentration or concentrations as a real time value.

The intensity of the light from the light sources may preferably be amplitude modulated at about 50 to 150 MHz. The second frequency of the second signal is of the same order, but differing from the first frequency typically by about 10 Hz to 100 KHz.

Typically, the light which is used is of a wavelength of about 650 nm to about 1300 nm, with at least three light sources of differing distances being present. However, it is preferred for at least six light sources of differing distances to be present, with the light sources being disposed in a pair of rows to provide pairs of light sources in the respective rows of the same distance from the sensor. This permits the simultaneous gathering of data at different light wavelengths, which different light wavelengths are emitted each by one of the rows of the sensors, for more accurate data gathering.

It is also preferred for each of the plurality of light sources to be sequentially activated (illuminated) for a length of time that is an exact multiple of a wave having a frequency which comprises the difference between the first and second frequencies as described above (the "cross correlation frequency").

Also, the information sensed by the light source may be summed and averaged from about eight to about eight hundred times of repetition, to obtain an intensified average of the photometric information received from each light source.

Typically, the method and apparatus of this invention make use of principles of frequency domain fluorometry and/or phosphorimetry which are well known, being disclosed for example in Gratton U.S. Pat. No. 4,840,485, Gratton et al. U.S. Pat. No. 5,212,386, and Gratton et al. application Ser. No. 07/983,829, filed Dec. 1, 1992, now U.S. Pat. No. 5,323,010 among others.

DESCRIPTION OF SPECIFIC EMBODIMENTS

Figure 1:
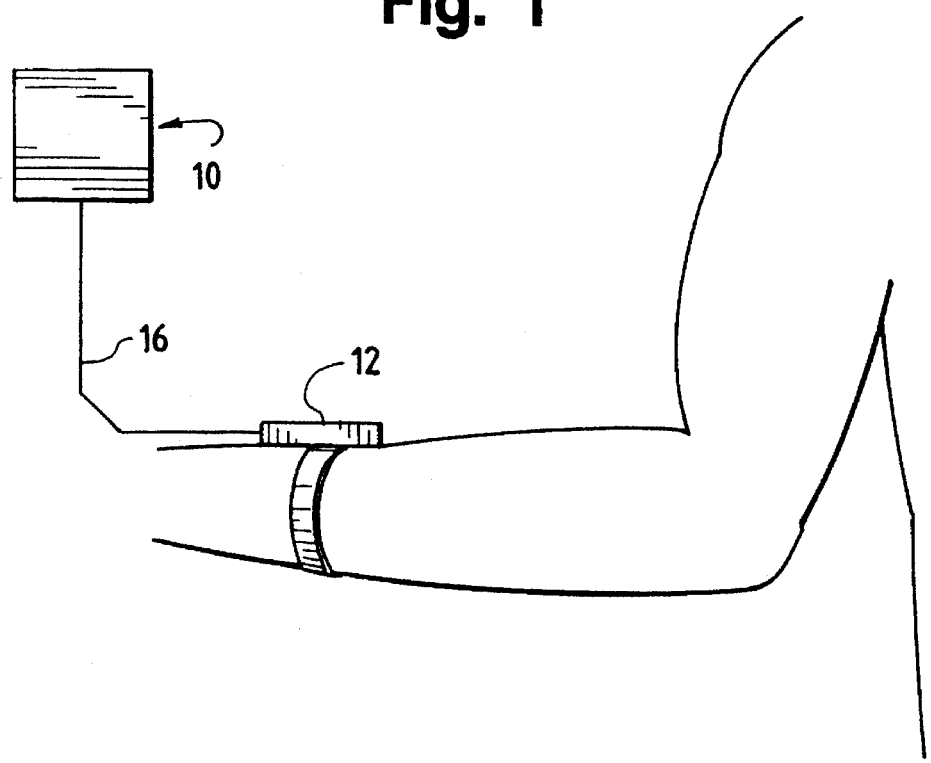
FIG. 1 is an elevational view of a sensor instrument used in the method of this invention, shown attached to the arm of a patient for sensing a component of body tissue.
Figure 2:
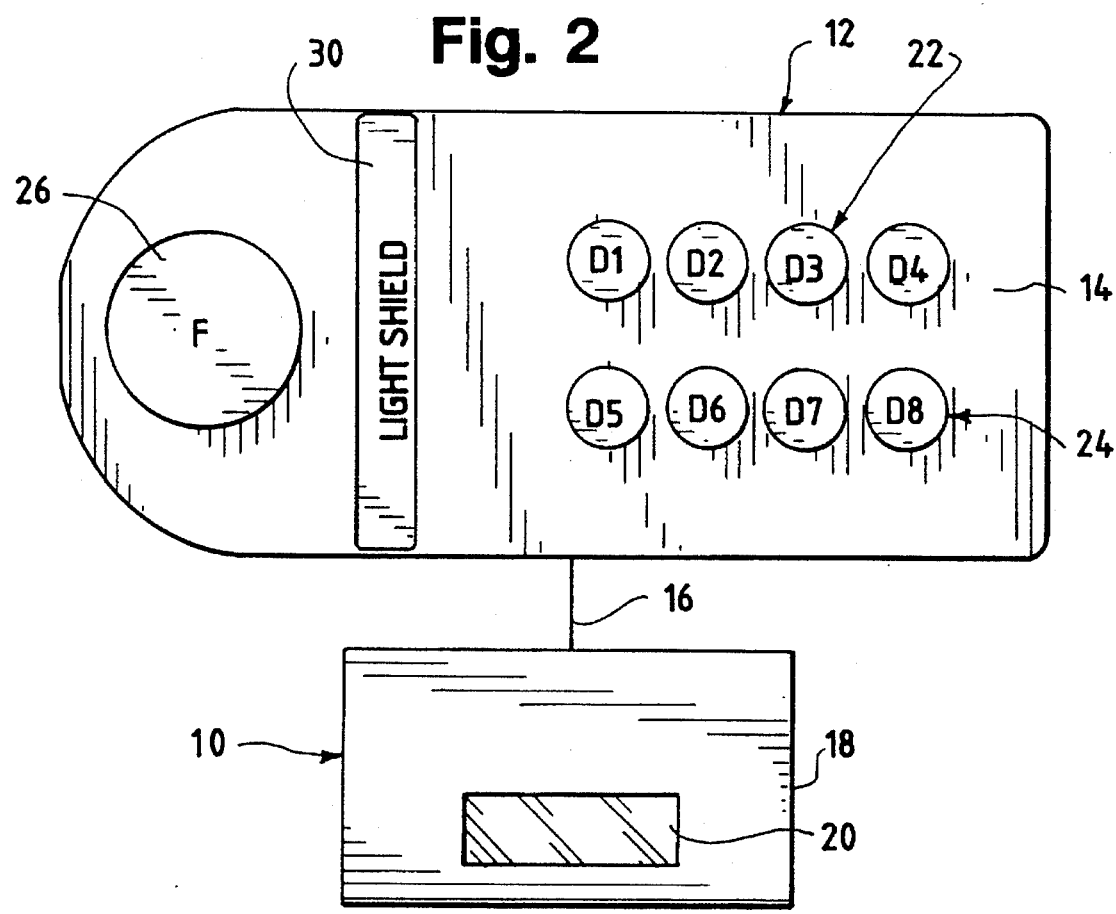
FIG. 2 is a schematic bottom plan view of the sensor instrument of FIG. 1, showing details of the sensor head.

In the drawings, a sensor instrument is shown for non-invasively and quantitatively determining the real time relative concentration of glucose or the like within living tissue of the patient. Sensor instrument 10 comprises a sensor head 12, which comprises a body having a sensor face 14 which may be flat or curved for better contact with the contour of a patient's arm, thigh, chest, or the like. Sensor 12 is placed with sensor face 14 in intimate contact with the skin of the patient. Cable 16 contains both an optical fiber and the electrical wires to convey both optical and electronic signals to processor unit 18. Alternatively, the light detector may be placed on the sensor head, and cable 16 is free of optical fibers. Data may be displayed at a readout window 20 in conventional manner.

Sensor head 12 carries eight light sources 22, 24 (individually labelled $D_1$–$D_8$) with four each of the respective light sources 22 and 24 being positioned in separate rows so that the respective light sources 22 and the respective light sources 24 are each at different distances from a conventional light sensor 26. Light sources 22, 24 may be light emitting diodes, laser diodes, or any other light source system which is capable of being amplitude modulated at the desired frequency range.

Figure 4:
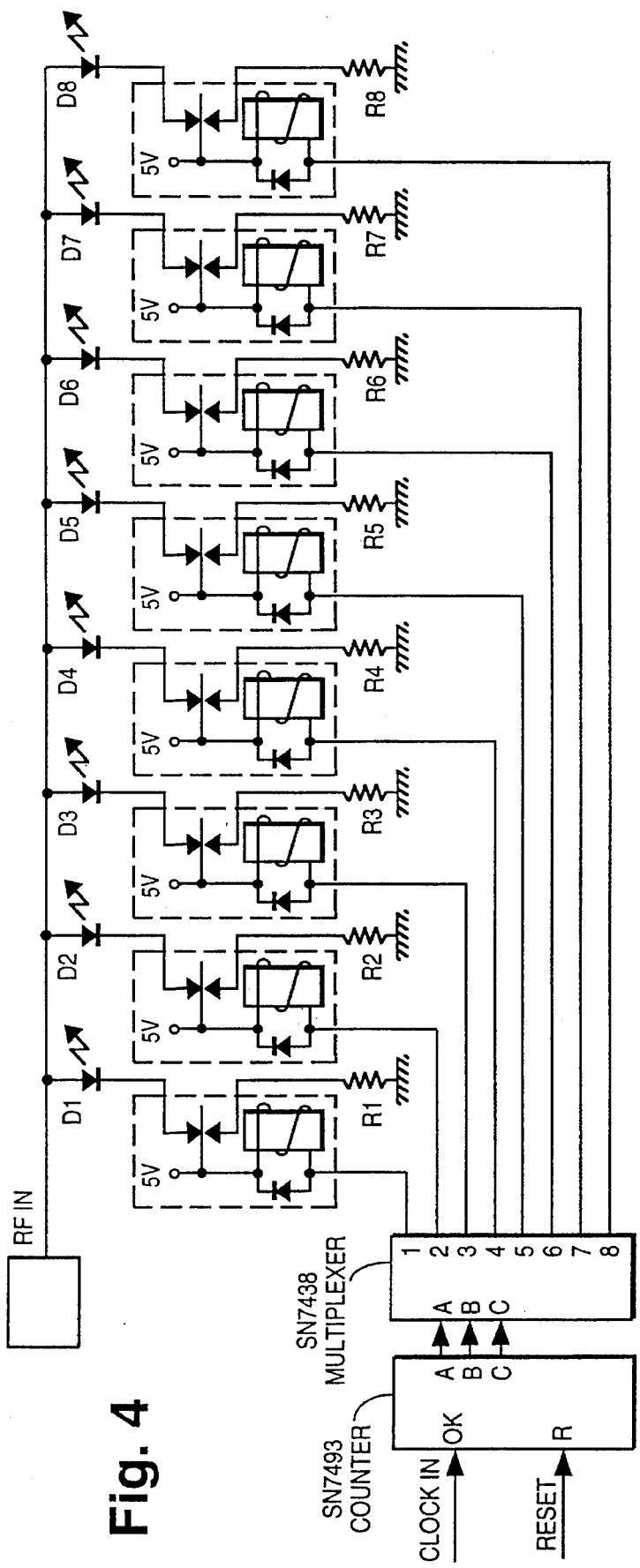
FIG. 4 is a diagram of a multiplexer circuit for turning the multiple light sources on and off in sequence, while causing the light emitted to be amplitude modulated at a high frequency.

By the multiplexer circuit of FIG. 4, the respective light sources 22, 24 are turned on and off, one at a time, in rapid succession. In this embodiment, the light sources are sinusoidally (amplitude) modulated at 120 MHz, to provide a frequency that maximizes the modulation of the source, and the sensitivity of the slopes (light intensity vs. distance) to the scattering and absorption coefficients. Also, detectors or sensors 26 having good sensitivity at this frequency are readily available.

Modulated light signals from the respective light sources 22, 24 enter the tissue of the patient, and travel in a highly scattered manner through the tissue of the patient to sensor 26. The direct transmission of light from each light source 22, 24 to sensor 26 without passing through tissue is prevented by a rubber light shield barrier 30, which projects slightly outwardly from face 14 of sensor head 12.

Figure 3:
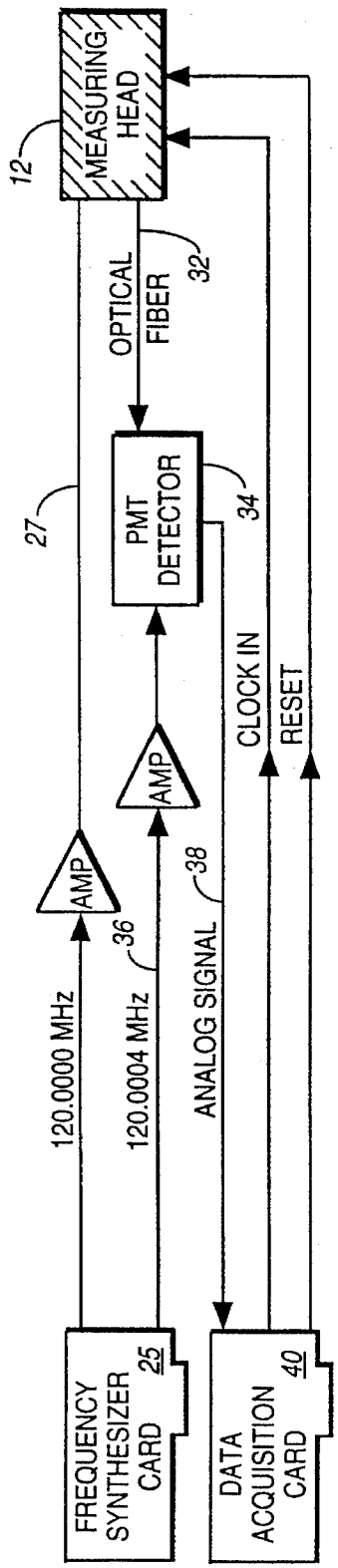
FIG. 3 is a block diagram of the electronics of the sensor instrument of the previous drawings.

The light passing through the tissue which is sensed by sensor 26 may be transmitted by an optical fiber 32 (FIG. 3), within connecting cable 16, which cable also carries wires, each communicating between sensor head 12 and processor unit 10. Light from optical fiber 32 passes to a photomultiplier detector 34.

Frequency synthesizer card 25 carries a frequency generator to provide an RF signal to head 12 and LEDs 22, 24 through wire 27 (also in cable 16), with conventional circuitry, to impose on the respective LEDs 22, 24 an amplitude modulation of 120.0000 MHz., which is the first frequency described above.

Frequency synthesizer card 25 also carries a frequency synthesizer which sends a second signal, coherent with the first but modulated at a second frequency, of 120.0004 MHz, through wire 36 to modulate the gain of photomultiplier detector 34. Thus, an analogue signal, which is a function of the signals through fiber 32 and wire 36, may be sent from detector 34 along wire 38 to data acquisition card 40. The particular analogue signal sensed by data acquisition card 40 may at be the "cross correlation frequency", which is the frequency of the difference between the first and second signals, or 400 Hz. in this example. This well established method produces a beating of the 120 MHz modulated current in the detector photomultiplier with the 120.0004 MHz radio frequency signal injected at the photomultiplier dynode, the photomultiplier output through wire 38 being modulated at the 400 Hz cross-correlation frequency. The radio frequency harmonics may be rejected by a low pass filter at an amplifier in detector 34.

Thus, each light source 22, 24 may be turned on for a length of time that is an exact multiple of the 400 Hz cross-correlation frequency wave period, i.e. for a length of time which is 2.5 milliseconds or a multiple thereof. In a typical measurement, a minimum of 8 to about a maximum of 800 periods of the 400 Hz wave are collected, depending on the light intensity through the tissue obtained at sensor 26. Each of these measuring periods may be digitized sixteen times. All of the collected waves of a measuring period may be averaged together, giving an average wave comprising 16 points, similar to the process described in Gratton et al. U.S. Pat. No. 5,212,386. Then, the 16 point wave may be transformed using a fast Fourier transform algorithm to give the value of the phase shift (P) component, the direct current (DC) component, and/or the alternating current (AC) component of the fundamental harmonic frequency of 400 Hz.

The above process can be repeated for each of light sources 22 and 24. The respective light sources 22 may emit at one wavelength such as 720 nm, and the other light sources 24 may emit at another wavelength such as 850 nm, to obtain a double set of data. Each of the respective light sources 22 are at different distances from sensor 26, as are each of the light sources 24, so that the data of each of the individual light sources of each set will be different, the more distant light sources exhibiting greater light attenuation through the tissue. The result of this can be a set of four values of the DC, AC, and phase shift (P) components at each wavelength, dependent on known distances of the light sources from the sensor.

Signals from the light detector 34 received by the data acquisition card 40 are digitized by the card (ISS A2D card, for example). A computer calculates from these data the respective slopes (S) of at least two of the DC, AC, and P components provided by each of the sets of lights 22, 24, since each of the respective lights provides differing values for the DC, AC, and P components, coupled with a known, constant distance of each light source from sensor 26. This can be accomplished as follows:

MATHEMATICAL BACKGROUND

In a frequency domain spectrometer the light intensity is sinusoidally modulated at a frequency f, generally in the 100 MHz region. The light source generates a photon density wave in the strongly scattering medium that propagates at a reduced velocity with respect to the velocity of light in water. This is due to the large number of collisions of the photons composing the photon density wave with the particles in the medium. At every point in space, the light intensity varies sinusoidally at the same frequency of the source, but it is phase shifted and attenuated with respect to the intensity of the source. The phase shift P and the attenuation of the sinusoidal modulated intensity AC and also of the average light intensity DC are a function of the distance from the source r and of the scattering ($\mu_s$) and absorption ($\mu_a$) coefficients, plus DC, AC and P values. The following relationship holds, when both light sources 22, 24 and detector 26 are placed on the surface of a large, uniform medium such as a patient's arm:

$$DC = \frac{DC_0 e^{-r\sqrt{2s}}}{r^2}$$

$$AC = \frac{AC_0 e^{-r\sqrt{s}\sqrt{x+1}}}{r^2}$$

$$P = P_0 + r\sqrt{s}\sqrt{x-1}$$

where $$s = \frac{3}{z} \mu_a(\mu_a + \mu_s)$$

$$x = \sqrt{y^2 + 1}$$

$$y = \frac{2\pi f}{v\mu_a}$$

In the above set of equations, the distance r between source and detector can be accurately measured independently. The first frequency of light modulation f is also exactly known, and v is the velocity of light in water. The only unknown parameters are the scattering and absorption coefficients, and phase, DC and AC factors of the modulated light.

The above equations require that we determine separately the value of the phase, DC and AC factors of the light. Rather than determining these quantities independently, it may be more practical to measure the values of the DC, AC and P at several distances r. The slopes of the plots of $\ln(r^2 DC)$, $\ln(r^2 AC)$ and P as a function of r provide quantities that are independent from the source constants. It is from these slopes that the scattering coefficient is measured in this particular implementation of the frequency domain spectrometer. By a measurement of any two of the above quantities, i.e., DC and P, AC and P and DC and AC, we can determine the optical parameters of the medium if we first determine the slopes of the plots defined above. Let us indicate with $S_{dc}$, $S_{ac}$, and $S_p$ the three slopes previously defined. The equations that relate $\mu_a$ and $\mu_s$ to the above slopes can be obtained from the following formulas:

$$\mu_a = \frac{2\pi f}{v} (x^2 - 1)^{-1/2}$$

$$\mu_s = \frac{s^2}{3\mu_a} - \mu_a \quad \text{(which may be used to determine imaging properties, see U.S. Pat. No. 5,213,105.}$$

(which may be used to determine imaging properties, see Pat. No. 5,213,105.

Thus, the absorption and scattering coefficients can be measured independently.

The symbols X and S are defined as follows for the 3 different pairs of possible measurements.
Using AC and phase measurements $$X = \frac{S_{ac}^2 + S_p^2}{S_p^2 - S_{ac}^2}$$

$$S = \sqrt{S_{ac}^2 - S_p^2}$$

Using DC and phase measurements $$X = \frac{S_{dc}^2 + 2S_p^2}{S_{dc}^2}$$

$$S = S_{dc}$$

and using DC and AC measurements $$X = \frac{2S_{ac}^2 - S_{dc}^2}{S_{dc}^2}$$

$$S = S_{dc}$$

Thus, $\mu_a$ and $\mu_s$ can be calculated by the above equations.

As stated above, any two out of the three slopes, once calculated as above by data acquisition card 40, may be used to electronically compute by card 40 the values of the scattering and absorption coefficients at each of the wavelengths used respectively by the lights 22 and 24. Preferably, the phase shift (P) slope and the DC slope are the values used for computing the scattering coefficient. From these values, the concentration of glucose or the like can be monitored in real time without drawing blood.

Figure 5:
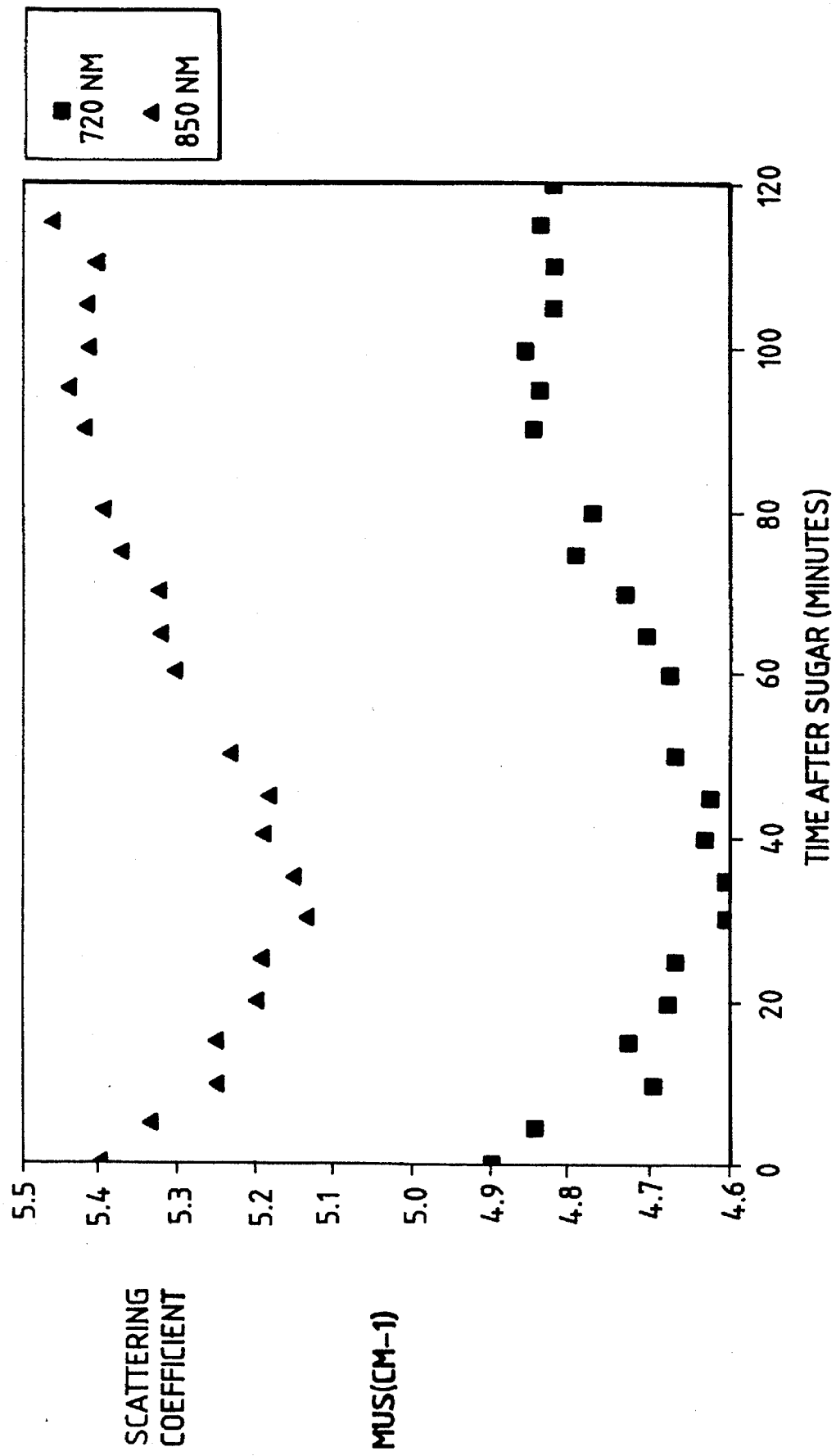
FIG. 5 is an exemplary graph showing how the apparatus of FIGS. 1–4 is capable of determining glucose levels non-invasively in a patient in real time.

Referring to FIG. 5, the graph shown represents the data obtained on a group of human volunteers. the volunteers drank an amount of glucose representing two grams of glucose per kg. of body weight. Then, using apparatus as described in this invention, the scattering coefficient was monitored at regular intervals for two hours, with a typical run being shown as FIG. 5. Two curves of data points are shown, the triangular data points being taken with infrared light at 850 nm and the lower data points being taken with infrared light at 720 nm.

As can be seen, the zero point time represents the original scattering coefficient achieved when the head 12 of the photometric unit is placed on the thigh of the patient. After ingestion of the glucose, the scattering coefficient drops substantially to a minimum, and then rises at a slower rate back to a value which is approximately the same as the original value. The slight "rebound" of the scattering coefficient at 850 nm may indicate a physiological response to the load of sugar, resulting in a slight decrease in the normal blood sugar level.

From these data, it can be seen that the blood glucose level of volunteers can be monitored on a real time basis by monitoring of the scattering coefficient of light passing through a portion of the body of the patient.

Figure 6:
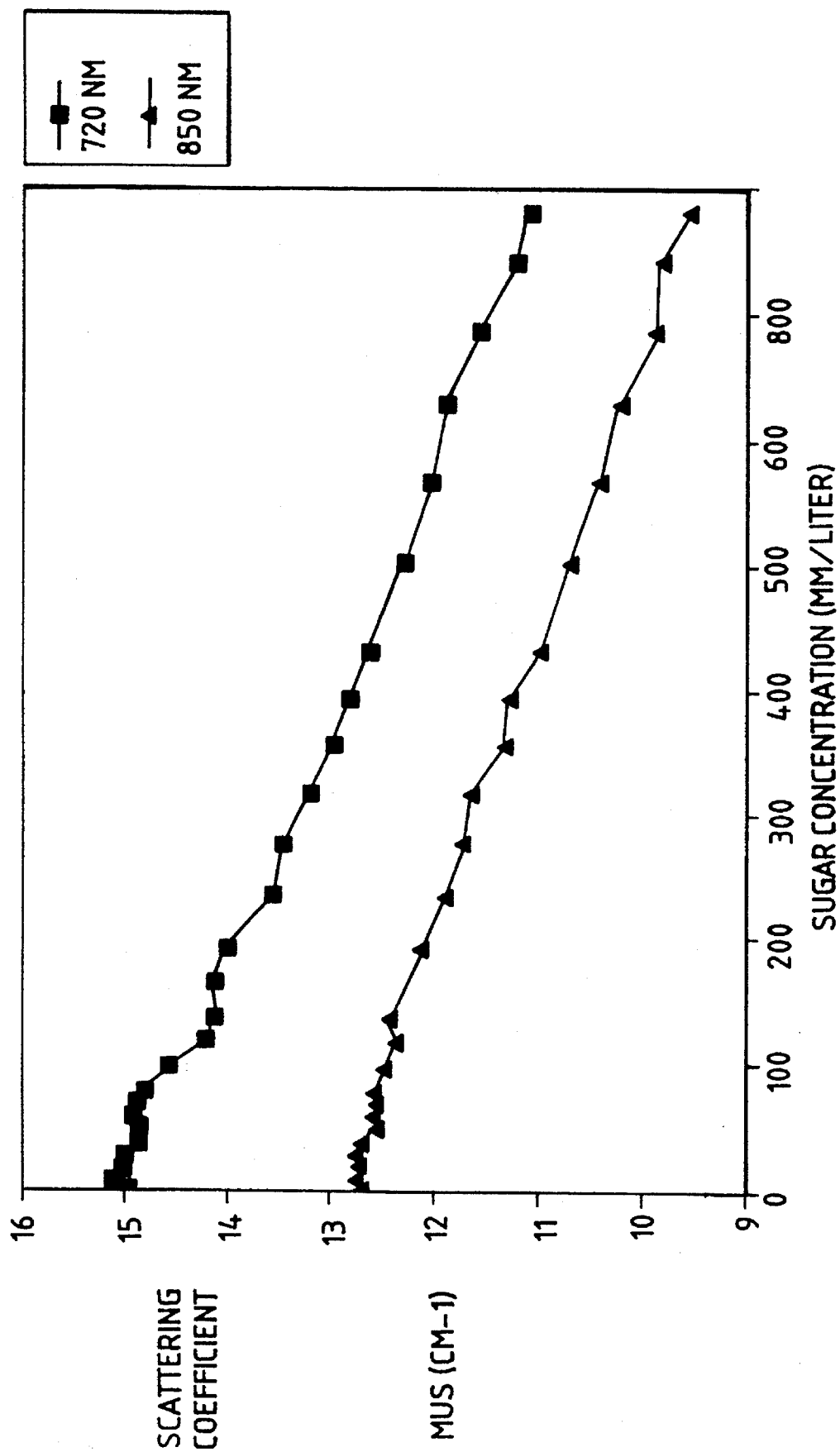
FIG. 6 is a graph showing the relation of the scattering coefficients at two wavelengths in an intravenous fat emulsion as the glucose concentration is increased.

Referring to FIG. 6, an intravenous fat emulsion (Intralipid brand fat emulsion) is provided with increasing concentrations of dissolved glucose as shown. The scattering coefficient of light through the fat emulsion-sugar solution was determined at a variety of known concentrations, and is shown to decrease in a predictable manner dependent upon the concentration of glucose present.

It is not necessary to use all of the light sources 22, 24 in every procedure of the apparatus of this invention. More light sources, for example 16 or 32 separate light sources, may be used. Also, a multiplexing principle may be applied to a much larger number of light sources, if desired, for the simultaneous determination of the concentration of more metabolites, or other metabolites from data which is more difficult to acquire. If a fewer number of light sources are used than 4 or 8, the rate of data acquisition can be increased accordingly. A higher acquisition rate can allow the determination of signals correlated with heart and breathing rhythms.

If desired, a pair of detector heads may be provided to process signals from differing detectors or sensors 26 positioned at different locations on the body, or at different sampling rates, so that fast and slow processes can simultaneously be measured.

Cross correlation frequencies used herein may typically vary from about 40 Hz to about 4000 Hz with relatively comparable results. The use of higher values for a crosscorrelation frequency allows better detection of faster processes.

While the light source multiplexer of FIG. 4 was constructed in this embodiment using mechanical relays, solid state switches may be used as a substitute if there is a desire to sequentially illuminate the respective lights 22, 24 at a rate faster than 2.5 milliseconds.

The respective light sources should be calibrated to give comparable light intensities at the detector 26. This may be done by the addition of series resistors to decrease the current in some of the light sources as needed. Light source equilibration permits the use of all the dynamic range of an analogue-to-digital converter, and may be done at the time of construction of the instrument.

However, it is desirable to periodically check the light source calibration for drifts over long use in the light source illumination characteristics. This calibration may be performed by placing head 12 on a solid block of a substance of known absorption and scattering coefficients, to determine the intensity of each light source as sensed by sensor 26. Note that this calibration procedure is different from the calibration of the present commercial oxymeters that need to be calibrated according to certain statistical tables based on the photometric characteristics of the particular tissue to be measured. The calibration that should be periodically accomplished in the instruments of this invention is a simple measurement of the light emission characteristics of the respective lights 22, 24, and nothing more.

The instrument shown permits direct, on screen, simultaneous monitoring in real time of several tissue parameters such as tissue glucose, tissue oxygen, and total blood volume.

The data obtained by this invention can also be used with different algorithms from that disclosed above to obtain desired information.

Both frequency synthesizer card 25 and data acquisition card 40 may basically be of the type described in the previously cited patents. Modifications of these cards for purposes of this invention may be readily accomplished by those skilled in the art.

The above has been offered for illustrative purposes only, and is not intended to limit the scope of the invention of this application, which is as defined in the claims below.

That which is claimed is:

1. A method of determining the relative concentration of a material in a turbid medium which comprises:

shining light through said turbid medium;

determining the scattering coefficient of said turbid medium using said light that has passed through the turbid medium;

comparing said scattering coefficient with a previous scattering coefficient of said turbid medium, whereby a change in said scattering coefficient indicates a change in the relative concentration of said material; and determining said relative concentration from said scattering coefficients.

2. The method of claim 1 in which said turbid medium is living, cellular tissue.

3. The method of claim 1 in which said turbid medium is an emulsion.

4. The method of claim 1 in which the wavelength of said light is from about 650 nm to about 1,300 nm.

5. The method of claim 1 in which said light shining through said turbid medium has an intensity and is provided by sequentially illuminating and shutting off a first group of light sources which each emit light of a first wavelength and which are spaced at different distances from a light sensor, while modulating the intensity of said light from said light sources at a first frequency, and in which a signal at a second frequency, coherent with said modulated light, is provided to said light sensor.

6. The method of claim 5 comprising modulating the gain of, or multiplying the output of, said light sensor by said coherent signal, said second frequency being different from said first frequency, and further deriving a resultant signal from the sensor while sequentially receiving said modulated light from said plurality of light sources through said turbid medium, said resultant signal being at a frequency of the difference between the first and second frequencies, to detect at least two of phase shift, DC, and AC components of said modulated light as sensed by the sensor, compared with the modulated light as originally emitted by the light sources.

7. The method of claim 6 comprising sequentially illuminating each of said plurality of light sources for a length of time that is an exact multiple of a wave period having a frequency which comprises the difference between said first and second frequencies.

8. The method of claim 7 comprising summing and averaging information sensed by said light sensor from each light source from about 8 to about 800 times to obtain an intensified average of the photometric information received from each light source.

9. The method of claim 8, wherein said shining step further comprises illuminating a second group of light sources which each emit light of a second different wavelength.

10. The method of claim 6, wherein said shining step further comprises illuminating a second group of light sources which each emit light of a second different wavelength.

11. The method of claim 1 in which said material is glucose.

12. A method of determining a tissue component concentration in a patient without drawing blood, which comprises placing an optical sensor head on the skin of the patient, said head carrying a first group of light sources and a light sensor, at least some of said light sources being at differing distances from said sensor and emitting light of a first wavelength, whereby pressing of said sensor against the skin permits the sensor to sense exclusively light from said light sources passing through tissue of the patient; passing light from said light sources in sequential manner through the tissue of said patient to the light sensor; determining the scattering coefficient of said tissue from said light that is passed through the tissue of said patient; comparing said scattering coefficient with a scattering coefficient previously obtained from the same portion of tissue, to obtain a relative concentration of said component of said tissue; and determining said relative concentration from said scattering coefficients.

13. The method of claim 12 in which the wavelength of said light is from about 650 nm to about 1,300 nm.

14. The method of claim 13 in which said light shining through said tissue has an intensity and is provided by sequentially illuminating and shutting off the first group of light sources which are spaced at different distances from a light sensor while modulating the intensity of said light from said light sources at a first frequency, and in which a signal at a second frequency, coherent with said modulated light, is provided to said light sensor.

15. The method of claim 14 comprising modulating the gain of, or multiplying the output of, said light sensor by said coherent signal of second frequency, said second frequency being different from said first frequency, and further deriving resultant signals from the sensor while sequentially receiving said modulated light from said first group of light sources through said tissue, said resultant signals being at a frequency of the difference between the first and second frequencies, to determine at least two of phase shift, DC, and AC components of said modulated light as sensed by the sensor, compared with the modulated light as originally emitted by the light sources.

16. The method of claim 15 comprising sequentially illuminating each of said first group of light sources for a length of time that is an exact multiple of a wave period having a frequency which comprises the difference between said first and second frequencies.

17. The method of claim 16 comprising summing and averaging information sensed by said light sensor from each light source from about 8 to about 800 times to obtain an intensified average of the photometric information received from each light source.

18. The method of claim 17, wherein said passing step further comprises illuminating a second group of light sources which each emit light of a second different wavelength.

19. The method of claim 12 in which said tissue component is glucose.

20. A method of determining the relative concentration of glucose in living cellular tissue which comprises:

shining light through said tissue for a first time and thereafter shining light through said tissue a second time;

determining the scattering coefficients of said light which is passed through said tissue during the first and second times, the wavelength of said light being substantially constant and from about 650 nm to about 1300 nm;

comparing the scattering coefficients, whereby a difference in said scattering coefficients indicates a change in the relative concentration of glucose present in said tissue; and determining said relative concentration from said scattering coefficients.

21. The method of claim 20 in which said light shining through said tissue has an intensity, and is provided by sequentially illuminating and shutting off a plurality of light sources, said light sources being spaced at different distances from a light sensor which senses light from said sources scattered in said tissue.

22. The method of claim 21 including the step of modulating the intensity of the light from said light sources at a first frequency, and in which a signal at a second frequency, coherent with said modulated light, is provided to said light sensor to modulate the gain or the output of said light sensor by said coherent signal, said second frequency being different from said first frequency, and further deriving a resultant signal from the sensor while sequentially receiving said modulated light by the sensor from said plurality of light sources through said tissue, said resultant signal being at a frequency of the difference between the first and second frequencies, to detect at least two of phase shift, DC, and AC components of said modulated light as sensed by the sensor.

23. The method of claim 22 in which a first group of said light sources emits light of a first wavelength, and in which a second group of said light sources emits light of a second, different wavelength, the light sources of each of said first group and said second group being spaced by differing distances from said sensor when compared with other light sources of its group.

24. A method of determining changing conditions in living tissue, which comprises: placing an optical sensor head on the skin of a patient, said head carrying a plurality of light sources and a light sensor, at least some of the light sources being at differing distances from the sensor and emitting light of essentially the same wavelength; sequentially activating and shutting off said light sources to cause the sensor to sequentially sense light from said sources passing through said tissue; determining the scattering coefficient from said light that has passed through said tissue; comparing said scattering coefficient with a previous scattering coefficient of said tissue; and determining said changing conditions from said scattering coefficients.

25. The method of claim 24 in which said changing conditions comprise changes in the concentration of a tissue component.

* * * * *